United States Patent [19]

Hanson

[11] Patent Number: 4,468,610

[45] Date of Patent: Aug. 28, 1984

[54] RADIO FREQUENCY APPARATUS FOR MEASURING MOISTURE CONTENT OF MATERIALS AS A FUNCTION OF DIELECTRIC CONSTANT

[75] Inventor: Colin J. Hanson, Valencia, Calif.

[73] Assignee: Penril Corp., Rockville, Md.

[21] Appl. No.: 368,427

[22] Filed: Apr. 14, 1982

[51] Int. Cl.³ ............................................. G01R 27/26
[52] U.S. Cl. .................................................... 324/61 R
[58] Field of Search ............................. 324/61 R, 61 P

[56] References Cited

U.S. PATENT DOCUMENTS

| | | | |
|---|---|---|---|
| 3,209,247 | 9/1965 | Mead et al. | 324/61 |
| 3,443,219 | 5/1969 | Adams | 324/61 R |
| 3,523,243 | 8/1970 | Wagner | 324/61 R |
| 3,723,865 | 3/1973 | Batey et al. | 324/61 R |

FOREIGN PATENT DOCUMENTS 0440615  1/1975  U.S.S.R. ............................ 324/61 R

*Primary Examiner*—Stanley T. Krawczewicz
*Attorney, Agent, or Firm*—Fleit, Jacobson, Cohn & Price

[57] ABSTRACT

Apparatus for measuring moisture content of gypsum board and like products as a function of dielectric constant comprising an rf signal source, an antenna disposed for rf field coupling to a test material, first and second reference inpedances, and a control circuit for selectively connecting the reference and antenna impedances to the output of the rf source. A rectifier is responsive to source output for providing the corresponding d.c. signal to measurement electronics. The measurement electronics first subtract a first reference signal indicative of the reference impedances from both a differing second reference signal indicative of the reference impedances and from a signal indicative of impedance at the antenna. Moisture content is then determined as a function of the ratio of the differences. A threshold detector is responsive to the difference between the antenna and reference signals for indicating the presence of test material adjacent the antenna.

8 Claims, 4 Drawing Figures

RADIO FREQUENCY APPARATUS FOR MEASURING MOISTURE CONTENT OF MATERIALS AS A FUNCTION OF DIELECTRIC CONSTANT

The present invention is directed to apparatus and systems for measuring physical characteristic of materials as a function of material dielectric characteristics, and more particularly to apparatus and systems of the described type which operate in the radio frequency range for measuring moisture content of gypsum board and like materials.

The patent to Mead et al U.S. Pat. No. 3,209,247 assigned to the assignee hereof discloses an apparatus for measuring moisture content of gypsum board which comprises an rf oscillator coupled to an antenna disposed so that test pieces are brought into the electric field generated by the antenna. Oscillator output voltage varies as a function of the dielectric constant of test materials coupled to the antenna, which in turn varies as a function of material moisture content. The oscillator output voltage is fed to recording and indicating means for indicating such moisture content to an operator. Limit switches are located adjacent the antenna and are responsive to movement of test material into proximity with the antenna for enabling operation of the recording and indicating functions. As a modification to the basic apparatus disclosed in Mead et al, the output voltage of the rf oscillator may be rectified to provide a d.c. voltage indicative of moisture content, which voltage may then be amplified by suitable circuitry, used in a closed-loop moisture control system and/or fed to suitable indicating or recording means.

The prior art apparatus so described has enjoyed substantial acceptance and success in the art. However, a number of problems have been noted which may have a deleterious effect upon system accuracy and reliability, and which therefore warrant improvement. For example, it has been found that output voltage of the rf oscillator, voltage drop across the oscillator output rectifier and/or amplification characteristics of the dc voltage amplifier circuitry may vary with temperature or other circuit operating conditions. Compensation for varying circuit parameters of these types is difficult and expensive. In addition, the limit switches disclosed in the Mead et al patent are often subjected in practice to environments which detract from limit switch operating lifetime, and therefore warrant repair more frequently than desired.

A general object of the present invention is to provide an apparatus or system for measuring a physical characteristic of materials as a function of material dielectric characteristics which improves upon or overcomes some or all of the aforementioned problems in the prior art.

A more specific object of the present invention is to provide an apparatus or system of the described type which automatically compensates for variations in electronic circuit characteristics caused by varying temperature or other circuit operating conditions.

Another specific object of the invention is to provide an apparatus or system of the described type in which presence of test material adjacent the antenna is detected electronically within the system electronics, and therefore which eliminates any requirement for mechanical limit switches as previously described.

A further object of the invention is to provide an improved system or apparatus which accomplishes the foregoing objects and which finds particular application for measurement of moisture content of gypsum board and other products of similar type as a function of dielectric constant.

The invention, together with additional objects, features and advantages thereof, will be best understood from the following description, the appended claims and the accompanying drawings in which:

Figure 1:
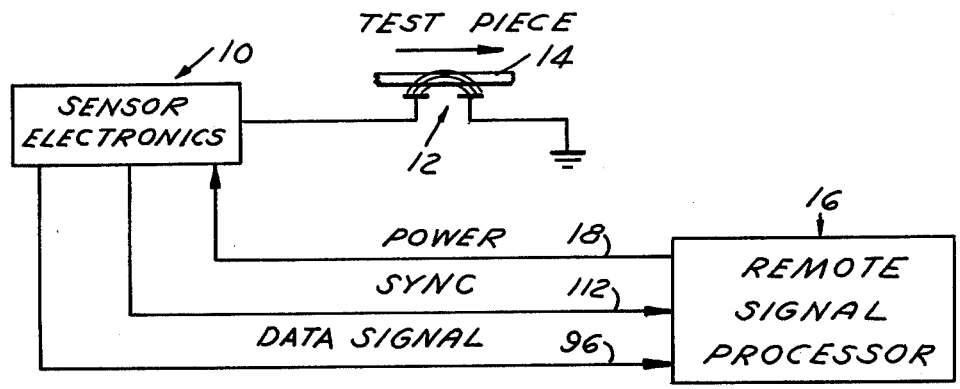
FIG. 1 is a functional block diagram of an overall system for measuring moisture content of a test piece in accordance with the present invention.

FIG. 1 illustrates a presently preferred embodiment of an overall system provided in accordance with the present invention as comprising a sensor electronics module 10 coupled to an antenna 12 disposed to be responsive to a test piece 14. Sensor electronics 10 is also connected to a remote signal processor 16 for receiving power therefrom on the conductors 18, and for providing data and synchronizing control signals thereto on conductors 96, 112 as a function of the measured physical characteristic of test piece 14. A presently preferred embodiment or application of the invention to be described in detail herein contemplates measurement of moisture content in test piece 14 as a function of test piece dielectric constant as sensed by antenna 12. Data signals indicative of moisture content and synchronizing control signals are fed by electronics 10 to processor 16 which may provide a suitable moisture measurement reading to an operator, feed such reading to storage for later analysis and/or drive closed loop control means for controlling drying of the test piece. Such indicating, storage and control means, as well as means for bringing test piece 14 into adjacent relationship with antenna 12, are well known in the art and are not shown in FIG. 1.

Figure 2B:
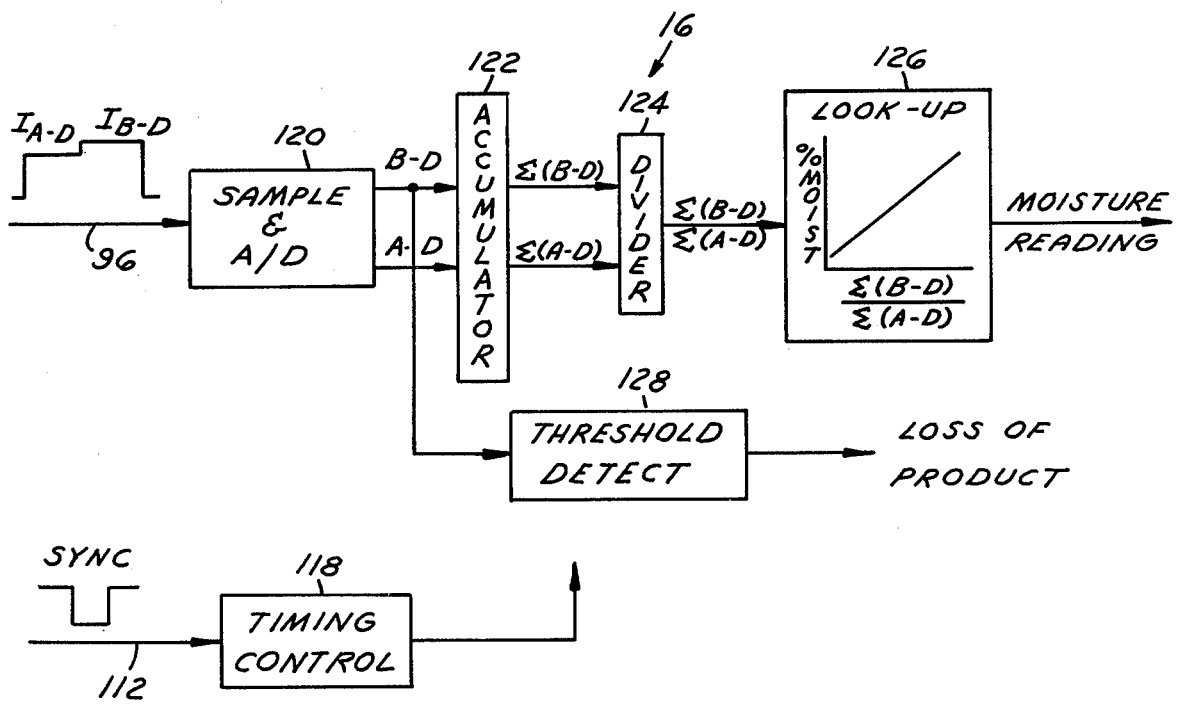
FIGS. 2A and 2B are semi-schematic and semi-functional block diagrams which together illustrate circuit details of a presently preferred embodiment of the system shown in FIG. 1.
Figure 2A:
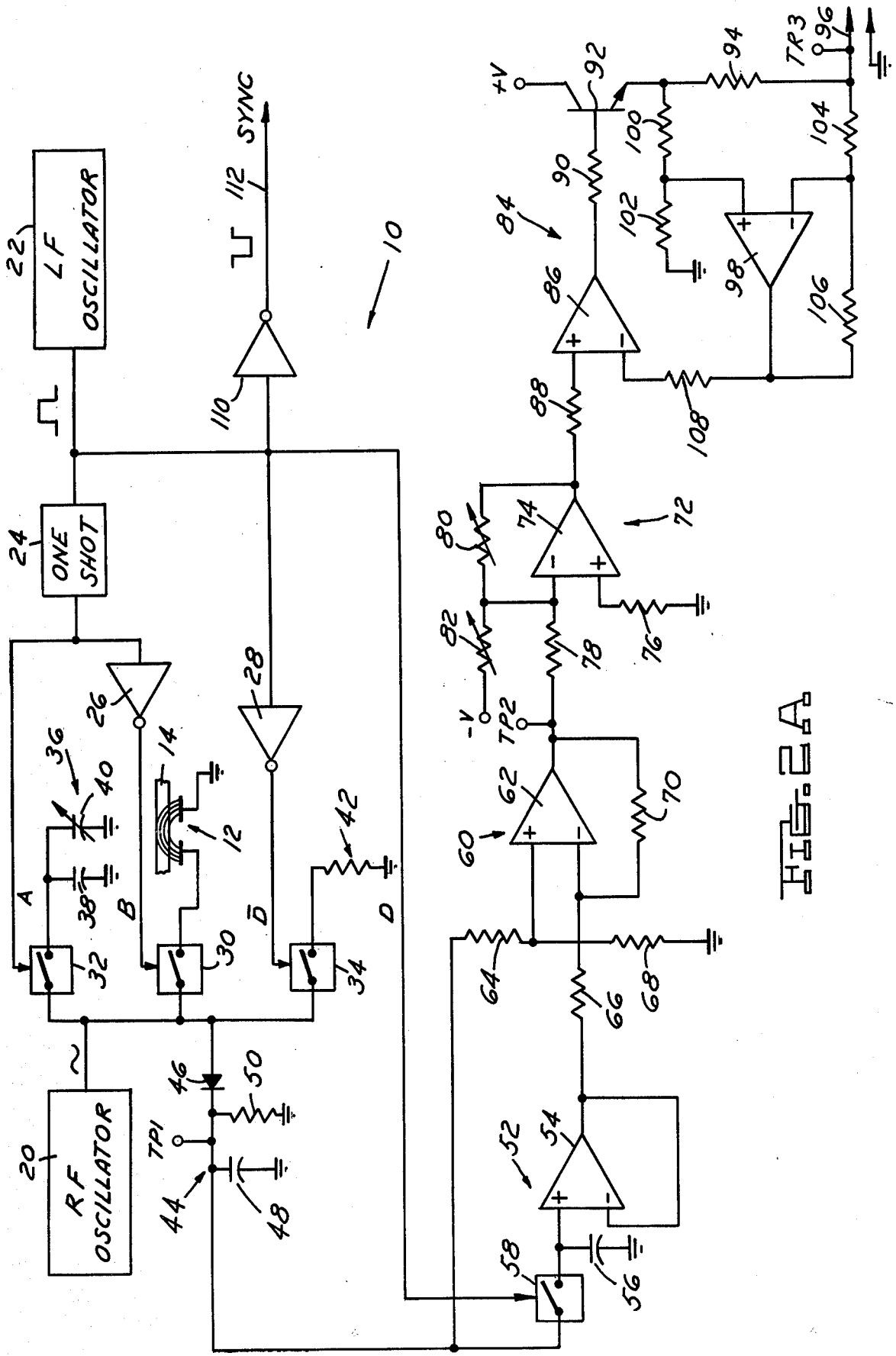

FIG. 2A illustrates a presently preferred embodiment of sensor electronics 10 as comprising an rf oscillator 20 which provides a sinusoidal output at a frequency of 2.5 megahertz, for example. A second oscillator 22 provides a pulsed output at low frequency as compared with the frequency of rf oscillator 20. In the particular example herein described oscillator 22 provides a pulse of two milliseconds duration every thirty-six milliseconds. A one-shot 24 has an input connected to the output of oscillator 22 and an output connected to the input of an inverter 26. A second inverter 28 has an input connected to the output of oscillator 22. The control signal outputs of one-shot 24, inverter 26, oscillator 22 and inverter 28 are designated A, B, D, and $\overline{D}$ respectively. Antenna 12 is connected to the output of rf oscillator 20 by a controlled electronic switch 30. A first reference impedance 36 is connected by a second electronic switch 32 between the rf oscillator output and ground, and comprises a fixed capacitor 38 connected in parallel with an adjustable capacitor 40. A second reference impedance comprising a fixed resistor 42 is connected by a third controlled electronic switch 34 between the rf oscillator output and ground. The control inputs of switches 30, 32, 34 are respectively connected to inverter 26, one-shot 24 and inverter 28 to receive the B, A and $\overline{D}$ control signals respectively. Switches 30, 32, 34 preferably comprise suitable FET switches.

A rectifier 44 is connected to the output of rf oscillator 20 to provide a dc signal indicative of voltage amplitude at the oscillator output. Rectifier 44 includes a diode 46 having an annode connected to the oscillator output. The parallel combination of a capacitor 48 and a resistor 50 is connected between the cathode of diode 46 and ground so as to provide across capacitor 48 the desired dc output indicative of oscillator output amplitude. A sample and hold circuit 52 includes a signal storage capacitor 56 connected across rectifier capacitor 48 by a controlled electronic switch 58 which receives a D control input signal from oscillator 22. Capacitor 56 is connected to the non-inverting input of a unity gain operational amplifier 54 which has an output connected to the inverting input. A differential amplifier 60 includes an operational amplifier 62 having a non-inverting input connected through a resistor 64 to the cathode of diode 46 and an inverting input connected through a resistor 66 to the output of amplifier 54. The non-inverting input of amplifier 62 is also connected to ground through a resistor 68, while the output thereof is connected to the amplifier inverting input by a resistor 70.

A voltage offset and scaling amplifier 72 comprises an operational amplifier 74 having a non-inverting input connected to ground through a resistor 76 and an inverting input connected to the output of amplifier 62 through the resistor 78. The output of amplifier 74 is connected to the inverting input by the factory-set resistor 80, and the inverting input is further connected to a negative reference voltage by the factory-set resistor 82. An output voltage-to-current amplifier 84 comprises a first operational amplifier 86 having a non-inverting input connected to the output of amplifier 74 through a resistor 88 and an output connected through the resistor 90 to the base of an NPN transistor 92. The collector of transistor 92 is connected to a positive voltage source, while the emitter is connected through a precision resistor 94 to provide on conductor 96 the data signal output to signal processor 16 (FIG. 1). A second operational amplifier 98 has a non-inverting input connected to the emitter of transistor 92 through a resistor 100 and to ground through a resistor 102. The inverting input of amplifier 98 is connected to conductor 96 through a resistor 104. The output of amplifier 98 is connected to the inverting input thereof through a resistor 106 and to the inverting input of amplifier 86 through a resistor 108. An inverter 110 receives an input from the output of oscillator 22 and provides the synchronizing control output signal SYNC on conductor 112 to signal processor 16 (FIG. 1). The SYNC signal from inverter 110 is identical to the $\overline{D}$ control signal.

Sensor electronics receive dc power and ground signals on conductors 18 (FIG. 1) as previously described. It will be appreciated that all amplifiers and inverters, one-shot 24 and oscillators 20, 22 are suitably connected to the dc supply voltages and to ground. Switches 30–34 and 58 are normally open as shown, and assume a closed conductive condition when the corresponding control input is a logical one. Oscillators 20, 22 are continuously operated during normal operation.

Figure 3:
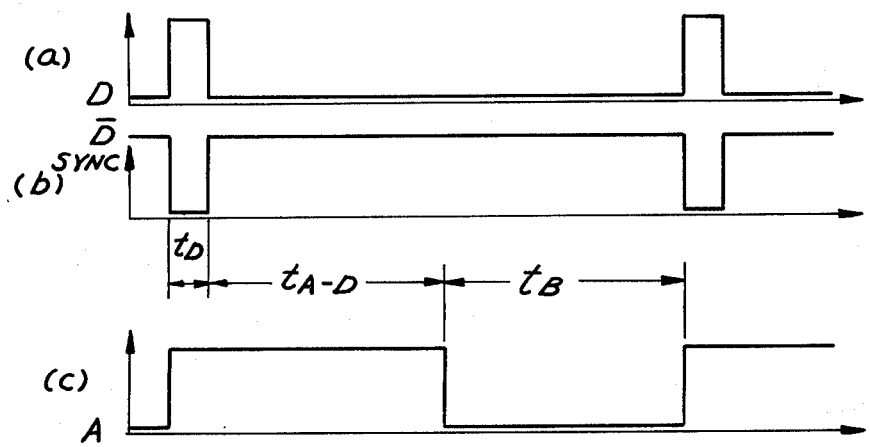
FIG. 3 is a timing diagram relating electrical signals in the system of FIGS. 2A and 2B, and which is useful in describing and understanding operation of the embodiment of the invention therein shown.
Figure 3:
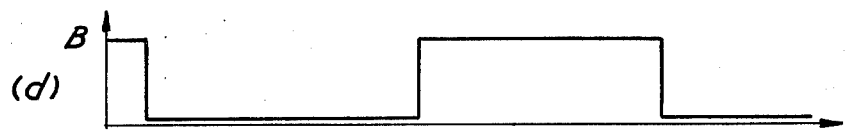
Figure 3:
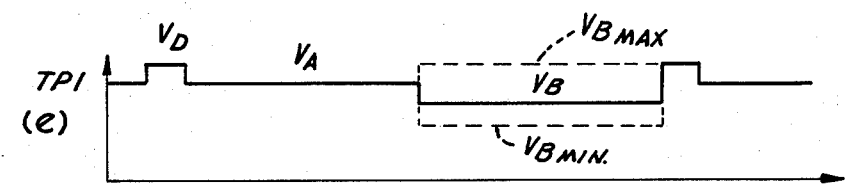
Figure 3:
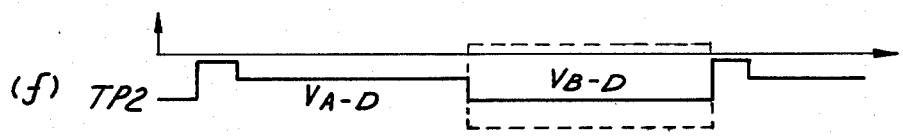
Figure 3:
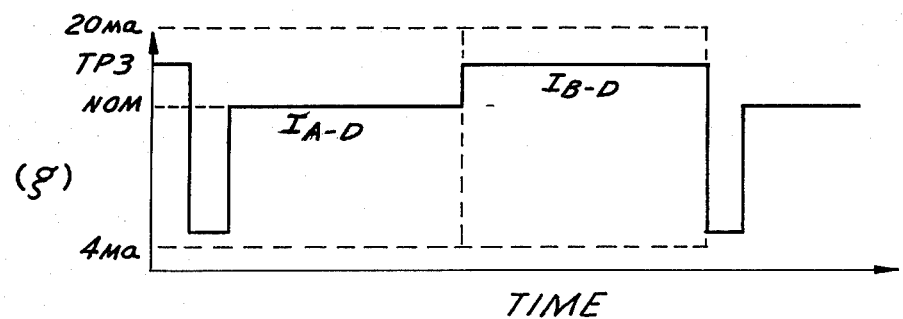

Operation of sensor electronics 10 (FIGS. 1 and 2A) will be best understood with reference to FIG. 3, which is a timing diagram showing relationships of control and data signals in the sensor electronics. Illustrations (a), (b), (c) and (d) in FIG. 3 illustrate control signals D, $\overline{D}$, A and B respectively. Transition of oscillator output D to a high state triggers one-shot 24 to provide a high A control signal. When one-shot 24 times out, the A control output goes low and the B control signal assumes a high state until the next D output from oscillator 22, whereupon the control cycle is repeated. Illustrations (a), (b), (c) and (d) thus show digital signals as a function of voltage versus time. Illustrations (e), (f) and (g) show the analog signals appearing at test points TP1, TP2 and TP3 in FIG. 2A for one cycle of operation. Test point TP1 is at the cathode of diode 46. Test point TP2 is at the output of amplifier 62. Test point TP3 is at the output of voltage-to-current amplifier 84 at conductor 96. Illustrations (e) and (f) show corresponding analog voltage versus time. Illustration (g) shows current versus time. Illustrations (a)–(g) have a common time scale.

Sensor electronics 10 operates selectively to connect first and second reference impedances 36, 42, and alternately to connect reference impedance 36 and antenna 12, to the output of oscillator 20 and to rectifier 44. More specifically, during the initial time $t_D$ of one operating cycle, reference impedance 36 is connected to oscillator 20 and rectifier 44 by switch 32, while switches 30, 34 remain open. Following termination of the D control signal, i.e. during the time $t_{A-D}$ when both A and $\overline{D}$ are high, reference impedances 36, 42 are connected in parallel across oscillator 20 by switches 32, 34. When the A output of one-shot 24 times out, the B control signal operates to connect antenna 12 to oscillator 20 through switch 30 for the remainder of the operating cycle. During this time $t_B$, switch 34 remains closed so that reference impedance 42 is in parallel with antenna 12, while switch 32 is open.

The following table summarizes the sequence in which the reference and antenna impedances are connected to oscillator 20 during each operating cycle:

$t_D$ . . . ref. imp. 36
$t_{A-D}$ . . . ref. imp's. 36, 42
$t_B$ . . . ref. imp. 42, antenna 12

Thus, the output voltage of oscillator 20 and the corresponding d.c. signal across rectifier capacator 48 varies during each portion of the control cycle as a function of impedance presented by the various reference and antenna loads on the oscillator output. The d.c. signal at test point TP1 is illustrated at (e) in FIG. 3. During time $t_D$, the voltage $V_D$ at TP1 is indicative of the load presented by reference inpedance 36 alone, while during the time $t_{A-D}$ the voltage $V_A$ is indicative of the greater load presented by impedances 36, 42 in parallel. Following initial set-up at the factory (to be described), and ignoring for the moment variations in circuit operating characteristics due to temperature, etc., voltages $V_D$ and $V_A$ remain constant. The d.c. voltage $V_B$ at TP1 during the time $t_B$ indicates the combined oscillator load presented by reference impedance 42 and antenna 12. $V_B$ thus varies with moisture content between a maximum when moisture content is low, reflected by a low impedance at antenna 12, and a minimum when moisture content is high.

During the time $t_D$ when control signal D is high, switch 58 operates to store the voltage $V_D$ on capacitor 56. Thus, during the time $t_D$, operational amplifier 62 functions effectively to subtract voltage $V_D$ at the output of amplifier 54 from voltage $V_D$ at capacitor 48, to yield an output voltage at TP2 which is substantially zero. During the next succeeding period $t_{A-D}$, the signal $V_{A-D}$ at TP2 is a function of voltage $V_A$ across capacitor 48 minus voltage $V_D$ stored on capacitor 56. Likewise, the voltage $V_{B-D}$ during the time $t_B$ is a function of voltage $V_B$ at TP1 minus voltage $V_D$ stored on capacitor 56. Amplifier 84 preferably provides to data signal conductor 96 a current of four milliamps for a desired minimum moisture reading value of $V_{B-D}$, and a current of twenty milliamps for a maximum expected moisture reading. This is accomplished by suitably setting or selecting resistors 80, 82 at the factory. See illustration (g) in FIG. 3. Reference capacitors 38, 40 are preferably factory selected and/or adjusted so that the output signal $I_{A-D}$ at TP3 indicative of impedance at antenna 12 is substantially equal to the signal $I_{B-D}$ for a nominal moisture content of the test piece, such as 10% moisture content for gypsum board.

Referring now to FIG. 2B, signal processor 16 includes a timing control circuit 118 which is responsive to the SYNC pulse from sensor electronics 10 to coordinate timing of the remainder of the processor electronics to be described. A sampling a/d converter 120 is responsive to timing control 118 to sample the analog d.c. signal $I_{A-D}$, $I_{B-D}$ from sensor electronics 10 at about the midpoint of the time periods $t_{A-D}$ and $t_B$ (FIG. 3), and to provide separate digital signals A–D, B–D to a digital accumulator 122 indicative the respective current levels. Accumulator 122 adds and stores each B–D and A–D signal to corresponding preceding signals from converter 120, and feeds the accumulated sums to a divider 124. The output of divider 124 is therefore an accumulated ratio of signal B–D divided by signal A–D. A look-up table 126, such as a read-only memory, is adapted to be programmed at the factory or in the field upon ititial installation so as to contain moisture measurement readings corresponding to ratios of B–D over A–D as accumulated and fed to the look-up table by divider 124. A moisture measurement reading corresponding to the accumulated ratio is provided as a processor output and fed to suitable storage, display and/or control means as previously described. The B–D output of converter 120 is also fed to a threashold detector 128. Reference impedance 42 (FIG. 2A) is preferably selected such that a B–D signal below a selected threshold indicates a loss of product adjacent antenna 12. A loss of product signal may be connected to control circuit 118 or otherwise used to control operation of the signal processor electronics and other storage, display and/or control means (not shown).

It will be appreciated that the use of two reference impedances for comparison to the antenna impedance, in conjunction with sensing moisture content as a function of a ratio of antenna to reference impedances, is effective to eliminate inaccuracies, etc. caused by temperature drift of the sensor electronics. More specifically, any change in amplitude of the output of oscillator 20, variation in voltage drop across rectifying diode 46, change in the dc reference voltages applied to amplifiers 54, 62, 74, 86 and 98, and/or variation in amplifier gain, will have equal effect on all of the analog reference and antenna signals. Thus, subtracting the $V_D$ reference signal from both the $V_A$ reference signal and the $V_B$ antenna signal effectively cancels the effects of such variations, so that the resulting ratio provides a reliable indication of moisture content. Additionally, the use of internal electronics to sense loss of product as a function of the reference and antenna signals eliminates the need for limit switches as hereinabove described, thereby providing a more economical and reliable indication of loss of product for control purposes.

It will be appreciated that the two reference impedances and the antenna impedance may be connected to the rf oscillator in sequences other than that disclosed. For example, the oscillator could be connected first to reference impedance 42 during the time period $t_D$, and then to reference impedance 36 and antenna 12 in turn during the time periods $t_{A-D}$ and $t_B$. It is considered preferable to insure that the reference dc voltages $V_D$, $V_A$ be unequal.

The invention claimed is:

1. Apparatus for measuring a physical characteristic of materials as a function of dielectric characteristics of said material comprising an rf oscillator, an rf antenna adapted to couple energy from said oscillator to the material, first and second reference impedance means, means for selectively connecting said oscillator during three discrete time intervals to said first reference impedance means and alternately to said second reference impedance means and said antenna such that output voltage of said oscillator varies during said three discrete time intervals as functions of said first and second reference impedance means and impedance at said antenna, rectifier means coupled to said output of said oscillator to provide a d.c. signal which varies as a function of said oscillator output during said three discrete time intervals, and means for providing an indication of said physical characteristic of said material as a combined function of said variable d.c. signal in each of said three discrete time intervals.

2. The apparatus as set forth in claim 1 wherein said means for providing said indication of said material characteristic comprises first means operable during one of said time intervals for obtaining a first reference signal as a function of said first and second reference impedance means and independent of said dielectric characteristics, second means operable during a second of said time intervals for obtaining a second reference signal different from said first reference signal as a function of said first and second reference impedance means and independent of said dielectric characteristics, third means operable during the third of said time intervals for obtaining a third signal indicative of said dielectric characteristics as a function of said impedance at said antenna, fourth means for providing a fourth signal as a function of a difference between said first and second signals, fifth means for providing a fifth signal as a function of a difference between said first and third signals, and sixth means for providing said indication of said physical characteristic as a function of a ratio between said fourth and fifth signals.

3. The apparatus as set forth in claim 2 wherein said first means comprises means operable during said one of said time intervals to sample and store said first signal, and wherein said fourth and fifth means comprise differential amplifier means having one input connected to said first means and a second input connected to said rectifier means for providing said fourth and fifth signals during said second and third time intervals respectively.

4. The apparatus as set forth in claims 2 or 3 wherein said sixth means comprises look-up table means relating said physical characteristic to differing values of said ratio.

5. The apparatus as set forth in claims 2 or 3 further comprising means responsive to said third signal for indicating proximity of material to said antenna.

6. Apparatus for measuring moisture content of a material as a function of material capacitance comprising an rf source having an output, means for providing control pulses indicative of three discrete time intervals, an antenna adapted to couple energy from said rf source to a test material, first and second reference impedance means, switch means responsive to said control pulses for selectively connecting said rf source output to said first and second reference impedance means during a first of said time intervals and alternately to said first reference impedance means and said antenna during second and third time intervals, rectifier means coupled to said source output to provide a d.c. signal which varies as a function of source output during said three time intervals, first means responsive to a difference in said d.c. signal during said first and second time intervals, second means responsive to a difference in said d.c. signals during said first and third time intervals, and means responsive to said first and second means for indicating moisture content of said material as a function of a ratio of said differences.

7. The apparatus as set forth in claim 6 wherein said first reference means comprises a capacitor having a capacitance characteristic equal to the capacitance characteristic of said antenna at a selected level of moisture content of said test material.

8. Apparatus for measuring a physical characteristic of materials as a function of dielectric characteristics of said material comprising first means including an rf source and an antenna for obtaining a first signal B as a function of dielectric characteristics of said material, second means coupled to said rf source for obtaining second and third signals A and D both independent of said dielectric characteristics of said material, said signals A and D being unequal, and means for determining said physical characteristic of said material as a function of a ratio of a difference between signals B and D to a difference between signals A and D.

* * * * *